US008389014B2

(12) United States Patent
Longo et al.

(10) Patent No.: US 8,389,014 B2
(45) Date of Patent: Mar. 5, 2013

(54) GEL USEFUL FOR THE DELIVERY OF OPHTHALMIC DRUGS

(75) Inventors: Antonio Longo, Rome (IT); Mose Santaniello, Nettuno (IT); Nicola Pescosolido, Rome (IT); Aleardo Koverech, Rome (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 771 days.

(21) Appl. No.: 12/517,445

(22) PCT Filed: Nov. 28, 2007

(86) PCT No.: PCT/EP2007/062929
§ 371 (c)(1),
(2), (4) Date: Jun. 16, 2009

(87) PCT Pub. No.: WO2008/077712
PCT Pub. Date: Jul. 3, 2008

(65) Prior Publication Data
US 2010/0069482 A1 Mar. 18, 2010

(30) Foreign Application Priority Data
Dec. 22, 2006 (EP) .................................. 06126981

(51) Int. Cl.
*A61K 9/50* (2006.01)
*A61K 9/14* (2006.01)
(52) U.S. Cl. ....................................... 424/501; 424/489
(58) Field of Classification Search .................. 424/400, 424/501, 489
See application file for complete search history.

(56) References Cited

U.S. PATENT DOCUMENTS

| 5,079,253 A * | 1/1992 | Hoyng et al. ............. 514/263.31 |
| 5,458,873 A | 10/1995 | Kawashima et al. |
| 6,258,847 B1 * | 7/2001 | Chachoua ..................... 514/562 |
| 2002/0035264 A1 | 3/2002 | Kararli et al. |
| 2003/0096012 A1* | 5/2003 | Besse et al. .................... 424/489 |
| 2004/0072809 A1* | 4/2004 | Demopulos et al. .......... 514/171 |
| 2005/0020502 A1* | 1/2005 | Metcalfe et al. ................ 514/16 |
| 2005/0042173 A1* | 2/2005 | Besse et al. ..................... 424/46 |

FOREIGN PATENT DOCUMENTS

| FR | 2679135 A1 | 1/1993 |
| WO | WO 0076506 A1 * | 12/2000 |

OTHER PUBLICATIONS

Herrero-Vanrell, et al., In vitro evaluation of solutions prepared from mucoadhesive polymers, Investigative Ophthalmolgy and Visual Science, 2005, 46:E-Abstract 2034.
Durrani, et al., Precorneal clearance of mucoadhesive microspheres from the rabbit eye, Journal of pharmacy and pharmacology, 1995, 47(7):581-584.

* cited by examiner

*Primary Examiner* — Sreeni Padmanabhan
*Assistant Examiner* — Gigi Huang
(74) *Attorney, Agent, or Firm* — Lucas & Mercanti, LLP

(57) ABSTRACT

The present invention relates to a solid powder composed of a mixture of a natural or a synthetic polymer which forms a gel, a buffer, such as an hydroxyacid or a dicarboxyacid, a saccharide, one or more drugs useful for the treatment of diseases of the eyes and optionally one or more excipients and/or regulators of the osmotic pressure ophthalmologically acceptable.

2 Claims, 3 Drawing Sheets

GEL USEFUL FOR THE DELIVERY OF OPHTHALMIC DRUGS

Figure 1:
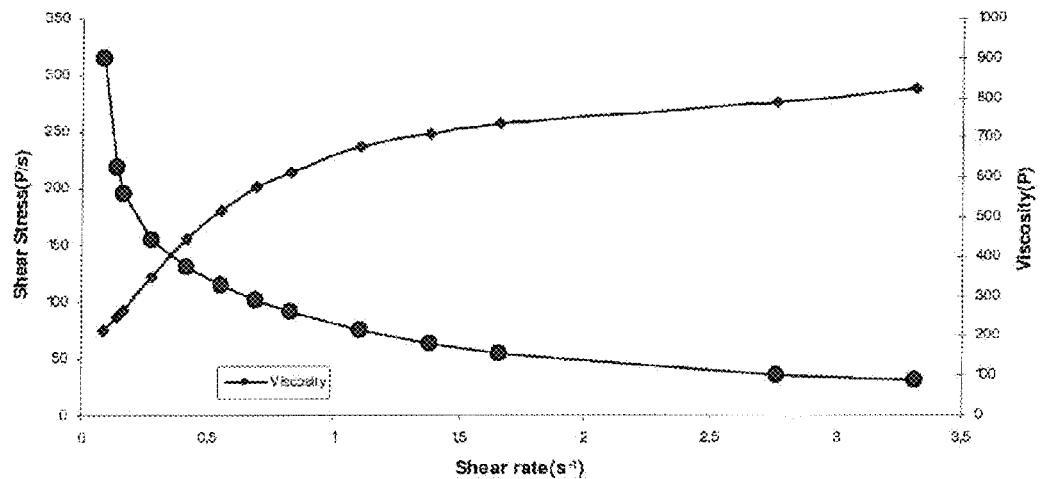

This application is a 371 of PCT/EP2007/062929 filed on Nov. 28, 2007, which claims the benefit of European Patent Application No. 06126981.7 filed on Dec. 22, 2006, the contents of each of which are incorporated herein by reference.

The present invention relates to a physiological supplement or medicament in the form of a solid powder which comprises a mixture of: a polymer which forms a gel, a buffer; a saccharide and one or more active ingredients useful for treating diseases of the eyes, in which said powder once is reconstituted with a suitable amount of water, or a liquid solution, provides a gel useful for the prevention or treatment of diseases of the eyes.

A non limiting example of diseases of the eye are cystinosys, dry eye syndrome, corneal oedema and diseases of the eyes due to ultraviolet radiation.

Cystinosis is a genetic metabolic disease that causes an amino acid, cystine, to accumulate in various organs of the body. Cystine crystals accumulate in the kidneys, eyes, liver, muscles, pancreas, brain and white blood cells. Without specific treatment, children with cystinosis develop end stage kidney failure at approximately age nine.

Cystinosis also causes complications in other organs of the body. The complications include muscle wasting, difficulty swallowing, diabetes, and hypothyroidism. It is estimated that at least 2,000 individuals worldwide have cystinosis, thought exact numbers are difficult to obtain because the disease is often undiagnosed and/or misdiagnosed.

The damage to the kidneys and other organs is thought to be due to accumulation of cystine inside the cells of various body tissues. This chemical also accumulates in the cornea and iris. After 10 to 20 years, the corneas of some patients become so packed with crystals that the surfaces may become irregular, occasionally causing small, painful breaks.

Treatment with cysteamine eye drops dissolve corneal cystine crystals and prevent damages of the eyes (N. Eng. J. Med. 347, 111-121; 2002).

Frequent instillation of concentrated solutions of cysteamine is necessary in order to achieve the desired therapeutic effects.

Dry eye syndrome is characterised by a quantitative (hypolacrimation) and/or qualitative (dyslacrimation) impairment of the tear film of multifactoral origin which may or may not cause clinically significant damage to the eye surface. The prevalence of dry eye syndrome ranges from 10 to 40% in the adult population and there is a highly significant correlation with age.

Oedema, or swelling, of the cornea occurs when the cornea is unable to keep itself clear and fluid begins to accumulate within it. The inside lining of the cornea is responsible for keeping it clear, and if this layer is damaged symptoms of corneal oedema may occur.

Causes of corneal oedema include disorders of the inside layer of the cornea such as Fuchs' endothelial dystrophy; eye surgery, such as cataract surgery; eye trauma; acute glaucoma with very high eye pressure; contact lens; infections.

Treatment of corneal oedema depends on its cause. Mild oedema can be treated with hypertonic eye drops and ointment. This draws fluid out of the cornea and into the tears, and helps to clear the cornea. More severe oedema, especially with blister (bullae) formation, may require corneal transplant to correct.

Ultra-violet radiation has long been recognized as a factor in the development of cutaneous cancer, aging of the skin, and mutagenic changes, it is only within the last decade or less that ultra-violet radiation has been universally recognized as a causative factor in ocular pathogenesis.

In humans, the eye has evolved into a sophisticated organ having neurophysiologic responses to photons in a certain portion of the electromagnetic spectrum, that provides a constant detailed map of the immediate environment. The action spectrum for these responses lie primarily within the 400-700 NM wavelength range, which has been labeled the visible spectrum or "Light".

Because solar UV radiation is present during most of the daylight hours, the eye may be exposed daily to some amount of solar ultraviolet radiation throughout life.

Diseases of the eye due to ultraviolet radiation include age-related cataract; pterygium; Macular Degeneration such as age related maculopathy (ARM), non age related maculopathy (nARM), age related macular degeneration (AMD); attinic photokeratitis and conjunctivitis.

Most of the conventional ophthalmic drug delivery systems encounter great problems due to unique physiological conditions of the eye, i.e., when a conventional liquid ophthalmic formulation is applied to the eye, upon instillation, it is immediately eliminated from the precorneal area of the eye because of lacrimal secretion and nasolacrimal drainage. As a result, only 1-10% of the ophthalmic drugs can be utilized by patients and a frequent instillation of concentrated solutions is necessary in order to achieve the desired therapeutic effects.

A drug to be applied topically on the eye is more effective if said drug remains in the eye in a time sufficient to exert its preventive or curative function. To lengthen the retention time of instilled ophthalmic drug in the eye and to enhance the bioavailability of the ophthalmic drug, various ophthalmic vehicles have been developed. Examples of such ophthalmic vehicles include various inserts, ointments, suspensions and gels. The ophthalmic vehicles known in the art have some drawbacks. For example, the use of ointments often causes blurred vision. Also, insert is not particularly popular among patients due to its low patient compliance.

Previous use of gel for ophthalmic use are already known.

Gurny et al., J. Contr. Release (1985), 2:353-361, discloses an ocular drug delivery system which includes cellulose acetophthalate (CAP) latex and Carbopol solution.

Rozier et al., Int. J. Pharm. (1989), 57: 163-168, discloses an ion-activated gelling vehicle with a trademark of Gelrite®. However, Rozier et al.'s gelling vehicle has the disadvantages of being converted into gel in the presence of mono- or divalent cations.

Joshi et al.'s U.S. Pat. No. 5,252,318 discloses reversibly gelling aqueous compositions which contain at least one pH-sensitive reversibly gelling polymer (such as carboxy vinyl linear or branched or cross-linked polymers of the monomers) and at least one temperature-sensitive reversibly gelling polymer (such as alkylcellulose, hydroxyalkyl cellulose, block copolymers of polyoxyethylene and polyoxypropylene, and tetrafunctional block polymers of polyoxyethylene and polyoxypropylene and ethylenediamine). Joshi et al.'s compositions exhibit significant changes in viscosity in response to substantially simultaneous changes in both temperature and pH.

Kumar et al., J. Ocular Pharmacol. (1994), 10: 47-56, discloses an ocular drug delivery system based on a combination of Carbopol and methylcellulose. The sol-gel transition of the combination occurs primarily due to an increase in pH because of the presence of Carbopol. Kumar et al., J. Pharm. Sci. (1995), 84: 344-348 (1995), discloses yet another ocular drug delivery system containing Carbopol and hydroxyproplymethylcellulose. In both systems, a viscosity-enhancing polymer is added to achieve a reduction in Carbopol concentration without compromising the in situ gelling properties as well as overall rheological behaviors.

Finkenaur et al.'s U.S. Pat. No. 5,427,778 discloses a gel formulations contains a polypeptide growth factor and a water soluble, pharmaceutically or ophthalmically compatible polymeric material for providing viscosity within various ranges determined by the application of the gel. Both Carbopol gels and Pluronic gels, respectively, are disclosed in the patent. Pluronic is the trademark for BASF's polyoxyethylene-polyoxypropylene block copolymers.

Viegas et al.'s U.S. Pat. No. 5,593,683 discloses a method for making a thermoreversible gels for drug or diagnostic agent delivery. The gels contain a pharmaceutical agent, a surfactant, and a polyalkylene polyether. The combined total amount of the surfactant and the polyalkylene polyether does not exceed about 10% by weight.

In the ophthalmologic field there is still a perceived need to have new vehicles useful for preparing medicaments for treating diseases of the eyes, not endowed with the drawbacks of the products known in the art.

It has now been found that a solid powder which comprises a mixture of a natural or synthetic polymer which forms a gel, a buffer, a saccharide, and a drug useful for the treatment of diseases of the eyes, in which said powder, once is reconstituted with a solution provides a gel suitable for ophthalmic administration.

The powder according to the present invention, respect to the gel present on the market presents the following advantages:

(a) is useful for preparing composition for the delivery of ophthalmic drugs which are not stable in solution;

(b) may not contain irritant preservatives.

In fact, it is well known that the eye drops and the gel for ophthalmic use present on the market contain preservative to avoid microbial contamination and said preservatives are irritant for the eyes (J. Am. Coll. Toxicol 8, 589-625; 1989).

The gel according to the present invention remains adherent to the eye, lengthens the retention time of instilled ophthalmic drug in the eye, and enhance the bioavailability of said ophthalmic drug.

It is therefore an object of the present invention a solid powder which comprises a mixture of:

a) a natural or synthetic polymers which forms a gel, an example of said polymer is a carboxy vinyl polymer such as Carbopol;

b) a buffer, such an hydroxyacid or a dicarboxylic acid selected from the group comprising phosphate, boric acetate, citrate, lactate, tartrate, maleate, succinate or fumarate;

c) a saccharide, selected from the group comprising glucose, fructose, mannitol, sorbitol, lactose, trehalose or maltose; and optionally d) one or more drugs useful for the treatment of diseases of the eyes.

The powder according to the present invention once reconstituted with water or a solution, provides a gel suitable for ophthalmic use.

It is a further object of the present invention a gel, useful for preparing a medicament for the treatment of diseases of the eyes, which comprises a mixture of:

a) a natural or synthetic polymers which forms a gel, an example of said polymer is a carboxy vinyl polymer such as Carbopol;

b) a buffer, such as an hydroxyacid or a dicarboxylic acid selected from the group comprising phosphate, boric acetate, citrate, lactate, tartrate, maleate, succinate or fumarate;

c) a saccharide, selected from the group comprising glucose, fructose, mannitol, sorbitol, lactose, trehalose or maltose; and d) one or more drugs useful for the treatment of diseases of the eyes. A non limiting example of said drugs is: cysteamine; pilocarpine; epinephrine; tetracycline; phenylephrine; eserine; timolo; L-carnitine and/or an alkanoyl L-carnitine selected from the group comprising: acetyl, propionyl, valeryl, isovaleryl, butyryl and isobutyryl L-carnitine, or an opthalmologically salt thereof; phospholine iodide; demecarium bromide; cyclopentolate; homatropine; scopolamine; chlortetracycline; bacitracin; neomycin; polymixin; gramicidin; oxytetracycline; chloramphenicol; gentamycin; penicillin; erythromycin; carbachol; sulfacetamide; polymixin B; idoxuridine; isoflorophate; fluoromethalone; dexamethasone; hydrocortisone; hydrocortisone acetate; 21-phosphate; fluorocinolone; medrysone; prednisolone; methyl prednisolone; prednisolone 21-phosphate; prednisolone acetate; betamethasone; triamcinolone; enzymes; vitamins; minerals; 3-Hydroxykynurenine O-β-DL-glucoside or a derivative thereof, citicholine; taurine; resveratrol, sodium jaluronate; or mixture thereof.

Preferred active ingredients are those which are not stable in water or in solution.

It is a further object of the present invention a method of preparation of the powder of the invention which comprises the following steps:

a) preparation of the gel dissolving in water the gelling agent, a buffer, a saccharide, and optionally one or more drugs useful for treating diseases of the eye;

b) the gel so obtained is divided in single doses and put into vials;

c) to obtain a powder the vials of step b) are lyophilized; alternatively the gel of point a) is directly subjected to Spray-drying procedure and the powder so obtained is put, in a suitable amount, into vials.

The powder so obtained before the use needs to be reconstituted with water or a solution.

It is a further object of the present invention a physiological supplement or medicament for ophthalmic use, which comprises the powder or the gel of the invention and one or more drugs useful for the treatment of diseases of the eyes; and optionally one or more excipients and/or regulators of the osmotic pressure opthalmologically acceptable.

It is a further object of the present invention a physiological supplement or medicament for ophthalmic use, which comprises the powder or the gel of the invention and as a drug (as active ingredient) cysteamine.

It is a further object of the present invention a physiological supplement or medicament for ophthalmic use, which comprises the powder or the gel of the invention and the following components:

L-carnitine, or an ophthalmically acceptable salt thereof, at a dose of 0.1-10%, a preferred dose is 1%;

taurine at a dose of 0.1-4%, a preferred dose is 0.5%;

sodium hyaluronate at a dose of 0.05-1.5%, a preferred dose is 0.2%;

vitamin E at a dose of 0.05-1.0%, a preferred dose is 0.2%;

manganese at a dose of 0.01-0.1 mg/L, a preferred dose is 0.051 mg/L;

zinc at a dose of 0.5-1.5 mg/L, a preferred dose is 1.02 mg/L;

sodium at dose of 5-5000 mg/L, a preferred dose is 30 mg/L;

potassium at a dose of 1-1000 mg/L, a preferred dose is 9 mg/L.

This physiological supplement or medicament is particularly useful for the treatment of dry eye syndrome.

It is a further object of the present invention a physiological supplement or medicament for ophthalmic use, which comprises the powder or the gel of the invention and the following components:

L-carnitine, or an ophthalmically acceptable salt thereof, at a dose of 5-15%; preferred dose is 10%;
taurine at a dose of 0.5-4%, a preferred dose is 2%;
sodium hyaluronate at a dose of 0.05-1.5%, a preferred dose is 0.2%;
vitamin E at a dose of 0.05-1.0%, a preferred dose is 0.2%;
manganese at a dose of 0.01-0.1 mg/L, a preferred dose is 0.051 mg/L;
zinc at a dose of 0.5-1.5 mg/L, a preferred dose is is 1.02 mg/L;
sodium at dose of 5-5000 mg/L, a preferred dose is 30 mg/L;
potassium at a dose of 1-1000 mg/L, a preferred dose is 9 mg/L.

This physiological supplement or medicament is particularly useful for the treatment of corneal oedema.

It is a further object of the present invention a physiological supplement or medicament for ophthalmic use, which comprises the powder or the gel of the invention and the following components:

L-carnitine, or an ophthalmically acceptable salt thereof, at a dose of 1-10%, a preferred dose is 5%;
3-Hydroxykynurenine O-$^3$-DL-glucoside 0.01-1 mg/mL, a preferred dose is 0.1 mg/mL;
Taurine at a dose of 0.5-4%, a preferred dose is 2%;
Resveratrol at a dose of 0.05-3 mg/mL, a preferred dose is 0.3 mg/mL;
Sodium jaluronate at a dose of 0.05-1.5%, a preferred dose is 0.2%;
Vitamin E at a dose of 0.05-1%, a preferred dose is 0.2%;
zinc at a dose of 0.5-1.5 mg/L, a preferred dose is 1.02 mg/L;
manganese at a dose of 0.01-0.1 mg/L, a preferred dose is 0.051 mg/L;
sodium at a dose of 5-5000 mg/L, a preferred dose is 30 mg/L;
potassium at a dose of 1-1000 mg/L, a preferred dose is 9 mg/L.

It is a further object of the present invention a physiological supplement or medicament for ophthalmic use, which comprises the powder or the gel of the invention and the following components:

acetyl L-carnitine, or an ophthalmically acceptable salt thereof, at a dose of 5-30%, a preferred dose is 20%;
3-Hydroxykynurenine O-$^3$-DL-glucoside at a dose of 0.01-1 mg/mL, a preferred dose is 0.1 mg/mL;
Vitamin E at a dose of 0.1-5%, a preferred dose is 1%;
Vitamin A at a dose of 15000-35000 UI, a preferred dose is 25000 UI.

This physiological supplement or medicament is particularly useful for the treatment of eye diseases due to ultraviolet radiation.

The physiological supplements or medicaments of the invention may further comprise one or more of the following active ingredients: antioxidants, vitamins, Borage oil; epithelialising and anti-angiogenic agents; citicholine, humidifying agents; inorganic elements; regulator of the cellular osmolarity; antibiotics; antiviral and antifungal agents; L-carnitine and/or one or more alkanoyl L-carnitines selected from the group consisting of acetyl, propionyl, valeryl, isovaleryl, butyryl and isobutyryl L-carnitine, or a pharmaceutically acceptable salt thereof.

The powder or the gel of the invention, when combined with one or more ophthalmic drugs, is useful for preparing a medicament for the treatment of diseases of the eye.

Further object of the present invention is a kit comprising the powder of the invention in admixture with one or more active ingredients (useful in the ophthalmic field) and, separately, in the same or in a different container/vial, water or a liquid solution suitable for obtaining the gel of the invention.

Further object of the present invention is a kit comprising:
a) the powder of the invention (not mixed with a drug useful for ophthalmic use);
b) one or more active ingredient useful for ophthalmic use (in liquid, solid, cream, gel or powder form); and
c) water or a liquid solution suitable for obtaining the gel of the invention; in which the (three) ingredients are into the same container/vial in separate space, and said (three) components can be easily mixed together to obtain the gel of the invention which may be directly administered on the eye.

The expert in container for ophthalmic use can easily suggest suitable containers which contains, for example, the gel mixed with one or more drugs; or a powder and separately (in the same container) a liquid; or 2 different powders and a liquid; for single or multiple applications. Different containers/vials are also included in the present invention.

What is meant by pharmaceutically acceptable salt of L-carnitine or alkanoyl L-carnitine is any salt with an acid that does not give rise to toxic or side effects.

These acids are well known to pharmacologists and to experts in pharmacy. Non-limiting examples of such salts are: chloride, bromide, orotate, aspartate, acid aspartate, acid citrate, magnesium citrate, phosphate, acid phosphate, fumarate and acid fumarate, magnesium fumarate, lactate, maleate and acid maleate, oxalate, acid oxalate, pamoate, acid pamoate, sulphate, acid sulphate, glucose phosphate, tartrate and acid tartrate, glycerophosphate, mucate, magnesium tartrate, 2-amino-ethanesulphonate, magnesium 2-amino-ethanesulphonate, methanesulphonate, choline tartrate, trichloroacetate, and trifluoroacetate.

What is meant by pharmaceutically acceptable salt of L-carnitine or alkanoyl L-carnitine is also a salt approved by the FDA and listed in the publication Int. J. of Pharm. 33 (1986), 201-217, which is incorporated herein by way of a reference.

DISCUSSION OF THE DRAWINGS

FIG. 1 shows shear stress and viscosity vs shear rates of the gel prepared in EXAMPLE 1. The gel resisted the initial rotary motion and a sudden increase in shear stress was observed at higher shear rate. The gel began to flow after shear stress reached its yield point. This system is a Newtonian flow of the pseudoplastic type with no hysteresis.

Figure 2:
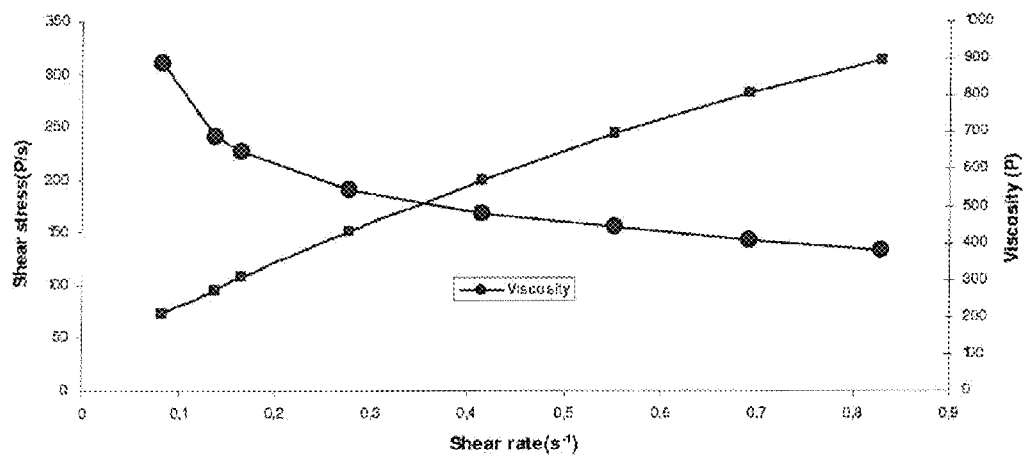

FIG. 2 shows shear stress and viscosity vs shear rates of the gel prepared in EXAMPLE 2. The gel resisted the initial rotary motion and a sudden increase in shear stress was observed at higher shear rate. The gel began to flow after shear stress reached its yield point. This system is a Newtonian flow of the pseudoplastic type with no hysteresis.

Figure 3:
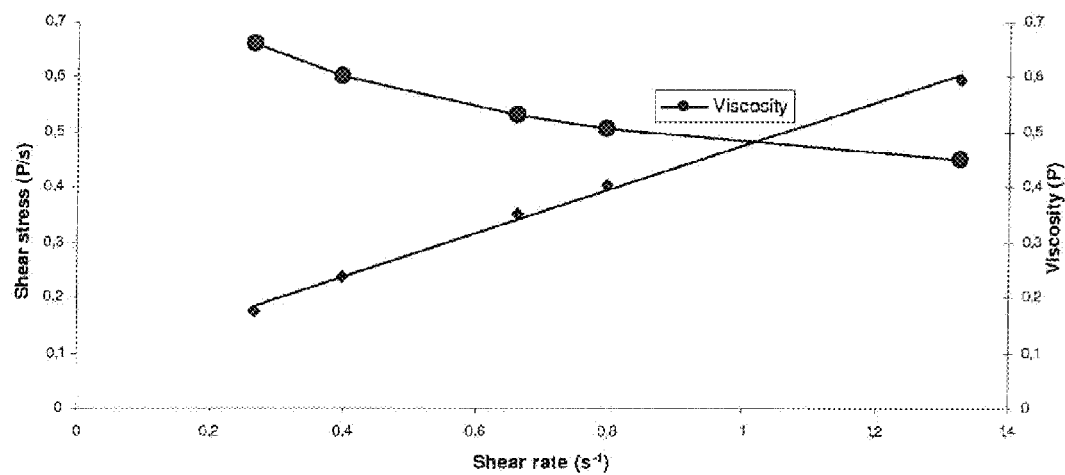

FIG. 3 shows shear stress and viscosity vs shear rates of the gel prepared in EXAMPLE 3. It can be observed with this gel that shear stress increases linearly with an increase in shear rate. This gelatinous system presents typical non-Newtonian flow behavior.

Figure 4:
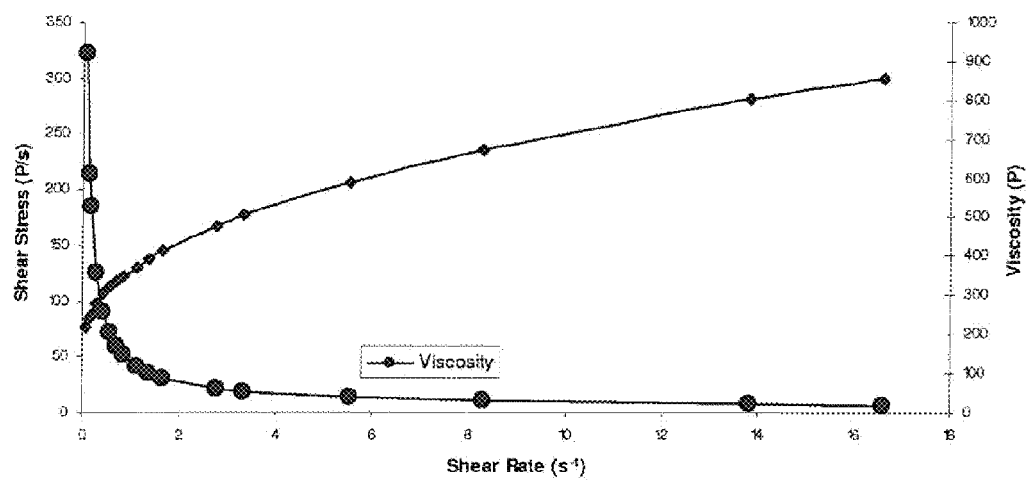

FIG. 4 shows shear stress and viscosity vs shear rates of the gel prepared in EXAMPLE 4. The gel resisted the initial rotary motion and a sudden increase in shear stress was observed at higher shear rate. The gel began to flow after shear stress reached its yield point. This system is a Newtonian flow of the pseudoplastic type with no hysteresis.

Figure 5:
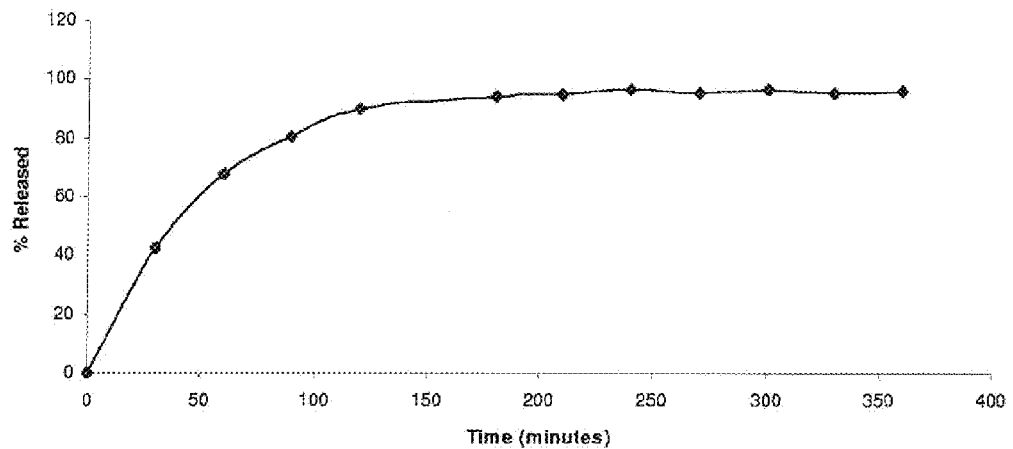

FIG. 5 shows the cumulative amount of cysteamine released vs time profiles for gel prepared as in EXAMPLE 1. The drug released about 42% into the medium after 30 min and then in gradual fashion. Approximately 96% of the cysteamine was released from the gel after 6 h.

Figure 6:
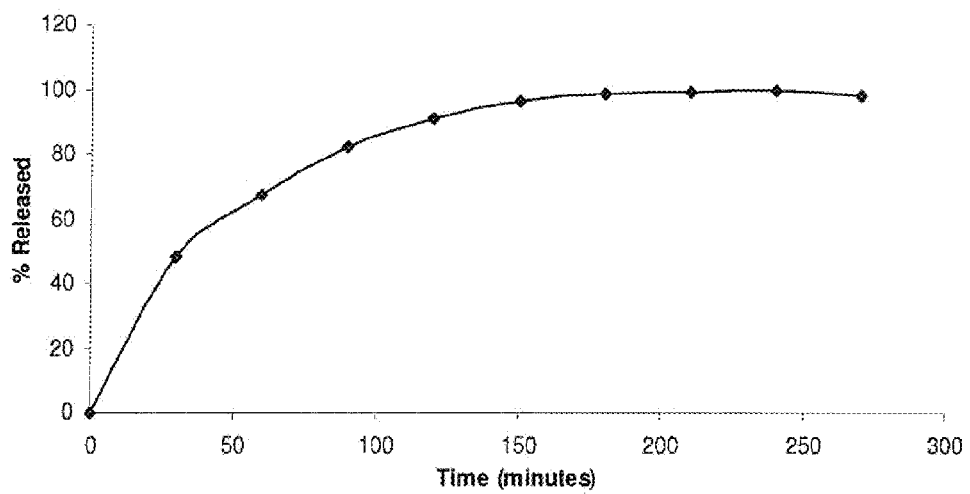

FIG. 6 shows the cumulative amount of cysteamine released vs time profiles for gel prepared as in EXAMPLE 2. The drug released about 46% into the medium after 30 min and then in gradual fashion. Approximately 98% of the cysteamine was released from the gel after 6 h.

The following examples are illustrative, but not limiting the scope of the present invention. Reasonable variations, such as those occur to reasonable artisan, can be made herein without departing from the scope of the present invention.

Materials

Carbopol 974P NF (Noveon), cysteamine and all other chemicals, including tartaric acid and benzalconium chloride, were purchased from Sigma and were used as received.

EXAMPLE 1

3 g of Carbopol 974P NF (Noveon) were slowly added to 190 mL of water containing 20 mg of benzalconium chloride, the solution was kept under stirring at room temperature for 18 h. Then, 500 mg of L-tartaric acid, followed by 6 g of mannitol and finally 1 g of cysteamine were added, keeping the solution under stirring until the cysteamine was completely solubilized.

The gelatinous system thus obtained was divided into fractions of 3 mL in 10-mL vials. Said vials were lyophilised for 24 h and a white solid was obtained.

Adding 3 mL of water to the lyophilized vial a gelatinous system having the following characteristics was readily obtained:

pH=4.0–4.3;

Osmotic pressure=229 mOsm/kg.

EXAMPLE 2

10 mg of benzalconium chloride and 500 mg of L-tartaric acid were added to 95 g of a 1.5% Carbopol 974P NF aqueous solution. A very fluid opalescent solution was obtained. To the opalescent solution were added 3 g of sorbitol and 1 g of cysteamine. The mixture so obtained was kept under stirring until the cysteamine was completely solubilized.

The gelatinous system thus obtained was divided into fractions of 3 mL in 10-mL vials. Said vials were lyophilised for 24 h and a white solid was obtained.

Adding 3 mL of water to the lyophilized vial a gelatinous system having the following characteristics was readily obtained:

Osmotic pressure=267 mOsm/kg;

pH=4.5–5.0.

EXAMPLE 3

1 g of L-tartaric acid was added to 95 g of a 1.5% Carbopol 974P NF aqueous solution, a very fluid opalescent solution was obtained. To this solution 3 g of sorbitol and 1 g of cysteamine were added, the mixture so obtained was kept under stirring until the is cysteamine was completely solubilized.

The gelatinous system thus obtained was divided into fractions of 3 mL in 10-mL vials. Said vials were lyophilised for 24 h and a white solid was obtained.

Adding 3 mL of water to the lyophilized vial a gelatinous system having the following characteristics was readily obtained:

pH=4.0–4.3

Osmotic pressure=297 mOsm/kg.

EXAMPLE 4

In 400 mL of water 3 g of Carbopol 974P NF, 2 g of tartaric acid, 6 g of lactose and finally 2 g of cysteamine in the sequence above reported, at room temperature, were dissolved. The slightly viscous solution, constantly kept under stirring was concentrated through a Spray-drying (Buchi B-191) under the following conditions: Inlet=60° C., ASP=82, Pump=0.06.

A white solid was obtained.

Adding 200 mL of water, to the white solid, a gelatinous system having the following characteristics was readily obtained:

pH=4.0–4.3

Osmotic pressure=225 mOsm/kg.

Rheological Studies

The rheological studies were carried out with a rotational viscometer of the concentric cylinder type (Viscometer TV-10 Toky Sangyo equipped with a small sample adapter and rotor type M3). The viscosity and shear stress of the samples were measured at various rates at 25° C. The temperature was maintained within +/−0.1° C. by a recirculating bath connected to the viscometer. The samples were equilibrated for five minutes to reach the running temperature prior to each measurement.

In Vitro Release Studies

In vitro release experiments were carried out with a dissolution instrument (Sotax AT 7 smart) equipped with a cell cream. Approximately 2 g of gel containing cysteamine prepared as reported in EXAMPLES 1 and 2 were weighed in the cell cream and placed in a 1000-mL vessel containing 500 mL of 50 mM acetate buffer, pH=4.5. The experiments were carried out at 37° C. and with a 50 rpm stirring paddle. At regular intervals, 1 mL of solution was withdrawn from the vessel and filtered using a 0.2 micron filter (Millez-FG Millipore) analyzed by HPLC to determine cysteamine concentration.

The HPLC chromatographic system composed of a pump (Waters 600); and autosampler (Waters 717); a UV detector (Waters 486) and integrator (Waters Empower 2). An inverse phase silica column (ODS-3 4.6×250 mm 5 micron) was used for the drug separation, pH=3, and as mobile phase was used a sodium dihydrogen phosphate buffer system. The flow rate and UV wavelength were 0.8 mL/min and 205 nm, respectively. The drug concentrations were determined by measuring the peak area in comparison with the peak area of known standards.

Carbopol® is a registered trademark of Noveon, Inc. (formerly B.F. Goodrich Co.) for a family of polymers that are used as thickeners, suspending agents and stabilizers.

L-carnitine and its alkanoyl derivatives are known compounds, the reparation process for which is described in U.S. Pat. No. 4,254,053.

3-Hydroxykynurenine O-$^3$-DL-glucoside is a product sold by Sigma-Aldrich, catalogue 2006; product code n° H1771.

The physiological supplement or medicament according to the present invention may be bought with or without medical prescription.

The physiological supplements or medicaments according to the present invention are composed of active ingredients which are familiar to operators in the medical field and already in use in clinical practice, and their pharmacotoxicological profiles are known.

Their procurement therefore is very easy, inasmuch as these are products which have been on the market now for a long time and are of a grade suitable for human or animal administration.

In the following are reported non limiting examples of composition according to the present invention.

Formulation 1

The powder or the gel of the invention and cysteamine.

This physiological supplement or medicament is particularly useful for the treatment of cystinosis.

Formulation 2

The powder or the gel of the invention and the following components (active ingredients):

| | |
|---|---|
| L-carnitine | 1%; |
| Taurine | 0.5%; |
| sodium hyaluronate | 0.2%; |
| vitamin E | 0.2%; |
| manganese | 0.051 mg/L; |
| zinc | 1.02 mg/L; |
| sodium | 30 mg/L; |
| potassium | 9 mg/L; |

Osmolality of about 125 mOsmols/kg.

This physiological supplement or medicament is particularly useful for the treatment of dry eye syndrome.

Formulation 3

The powder or the gel of the invention and the following components:

| | |
|---|---|
| L-carnitine | 10% |
| taurine | 2% |
| sodium jaluronate | 0.2% |
| vitamin E | 0.2% |
| zinc | 1.02 mg/L |
| manganese | 0.051 mg/L |
| sodium | 30 mg/L |
| potassium | 9 mg/L |

Osmolality of about 1200 mOsmols/kg.

This physiological supplement or medicament is particularly useful for the treatment of corneal oedema.

Formulation 4

The powder or the gel of the invention and the following components:

| | |
|---|---|
| L-carnitine | 5% |
| 3-Hydroxykynurenine O-β-DL-glucoside | 0.1 mg/mL |
| Taurine | 2% |
| Resveratrol | 0.3 mg/mL |
| Sodium jaluronate | 0.2% |
| Vitamin E | 0.2% |
| zinc | 1.02 mg/L |
| manganese | 0.051 mg/L |
| sodium | 30 mg/L |
| potassium | 9 mg/L |

This physiological supplement or medicament is particularly useful for the treatment of eye diseases due to ultraviolet radiation.

Formulation 5

The powder or the gel of the invention and the following components:

| | |
|---|---|
| Acetyl L-carnitine | 20% |
| 3-Hydroxykynurenine O-β-DL-glucoside | 0.1 mg/mL |
| Vitamin E | 1% |
| Vitamin A | 25000 UI. |

This physiological supplement or medicament is particularly useful for the treatment of eye diseases due to ultraviolet radiation.

The invention claimed is:

1. A solid powder consisting of:
   a carboxy vinyl polymer as a gelling agent;
   a buffer which is a hydroxyacid or a dicarboxylic acid selected from the group consisting of phosphate, boric acetate, citrate, lactate, tartrate, maleate, succinate and fumarate buffer;
   a saccharide selected from the group consisting of glucose, fructose, mannitol, sorbitol, lactose, trehalose and maltose; and cysteamine;
said solid powder providing a gel suitable for ophthalmic use when reconstituted with water.

2. The solid powder according to claim 1 wherein the carboxy vinyl polymer is carbopol.

* * * * *